(12) United States Patent
Newman

(10) Patent No.: US 9,395,337 B2
(45) Date of Patent: Jul. 19, 2016

(54) NONDESTRUCTIVE ACOUSTIC DOPPLER TESTING OF WIND TURBINE BLADES FROM THE GROUND DURING OPERATION

(71) Applicant: DIGITAL WIND SYSTEMS, INC., Newtown Square, PA (US)

(72) Inventor: John W. Newman, Newtown Square, PA (US)

(73) Assignee: Digital Wind Systems, Inc., West Conshohocken, PA (US)

( * ) Notice: Subject to any disclaimer, the term of this patent is extended or adjusted under 35 U.S.C. 154(b) by 636 days.

(21) Appl. No.: 13/840,470

(22) Filed: Mar. 15, 2013

(65) Prior Publication Data

US 2014/0278151 A1   Sep. 18, 2014

(51) Int. Cl.
| | |
|---|---|
| *G01N 29/11* | (2006.01) |
| *G01N 29/14* | (2006.01) |
| *F03D 11/00* | (2006.01) |

(52) U.S. Cl.
CPC ............ *G01N 29/11* (2013.01); *F03D 11/0091* (2013.01); *G01N 29/14* (2013.01); *F05B 2270/81* (2013.01); *Y02E 10/722* (2013.01); *Y02E 10/726* (2013.01)

(58) Field of Classification Search
CPC .... F03D 11/0091; G01N 29/11; G01N 29/14; F05B 2270/81
See application file for complete search history.

(56) References Cited

U.S. PATENT DOCUMENTS

| | | | |
|---|---|---|---|
| 3,371,212 A | 2/1968 | Weiss | |
| 3,478,353 A | 11/1969 | Adams, Jr. | |
| 3,810,005 A | 5/1974 | Bennion et al. | |
| 3,922,907 A | 12/1975 | Hurwitz et al. | |
| 4,413,519 A | 11/1983 | Bannister et al. | |
| 4,507,658 A | 3/1985 | Keating | |
| 5,146,289 A | 9/1992 | Newman | |
| 5,257,088 A | 10/1993 | Tyson, II et al. | |
| 5,471,880 A * | 12/1995 | Lang ..................... | G01H 1/006 702/56 |
| 5,479,826 A | 1/1996 | Twerdochlib et al. | |
| 5,481,356 A | 1/1996 | Pouet et al. | |
| 5,543,916 A | 8/1996 | Kachanov | |
| 5,748,003 A | 5/1998 | Zoughi et al. | |
| 5,818,242 A | 10/1998 | Grzybowski et al. | |
| 5,923,425 A | 7/1999 | Dewa et al. | |

(Continued)

FOREIGN PATENT DOCUMENTS

| | | | |
|---|---|---|---|
| DE | EP 2131037 A2 * | 12/2009 | ............ F03D 7/0296 |
| EP | 2131037 A2 | 12/2009 | |

(Continued)

OTHER PUBLICATIONS

Daniel, Monitoring the operation of a wind energy plant by sound analysis, Dec. 9, 2009, EP2131037.*

(Continued)

*Primary Examiner* — John Breene
*Assistant Examiner* — Mohammad Islam
(74) *Attorney, Agent, or Firm* — Panitch Schwarze Belisario & Nadel LLP

(57) ABSTRACT

A wind turbine blade inspection system includes a sensitive microphone positioned near the base of the turbine tower to receive acoustic signals emanating from anomalies in a rotating turbine blades and a signal analysis system configured to analyze the acoustic signals including Doppler analysis. The data may be centrally monitored and recorded for wind power asset management.

13 Claims, 9 Drawing Sheets

(56) References Cited

U.S. PATENT DOCUMENTS

| | | | |
|---|---|---|---|
| 6,153,889 | A | 11/2000 | Jones |
| 6,246,483 | B1 | 6/2001 | Smith et al. |
| 6,394,646 | B1 | 5/2002 | Ringermacher et al. |
| 6,448,924 | B1 | 9/2002 | Hafer, Jr. |
| 6,674,531 | B2 | 1/2004 | Mahner |
| 6,717,681 | B1 | 4/2004 | Bard et al. |
| 6,881,507 | B2 | 4/2005 | Milacic |
| 6,891,148 | B1 | 5/2005 | Rivera et al. |
| 6,966,754 | B2 * | 11/2005 | Wobben ............. F03D 11/0091 415/118 |
| 6,968,730 | B2 | 11/2005 | Schafrik et al. |
| 7,019,537 | B2 | 3/2006 | Hazel et al. |
| 7,083,327 | B1 | 8/2006 | Shepard |
| 7,083,384 | B2 | 8/2006 | Bosselmann et al. |
| 7,095,221 | B2 | 8/2006 | Bosselmann et al. |
| 7,225,548 | B2 * | 6/2007 | Sieracki ................ G02B 23/00 33/267 |
| 7,283,251 | B1 | 10/2007 | Tansey |
| 7,432,505 | B2 | 10/2008 | Brummel |
| 7,554,324 | B2 | 6/2009 | Gualtieri |
| 7,825,669 | B2 | 11/2010 | Parsons et al. |
| 7,889,119 | B2 | 2/2011 | Evers et al. |
| 8,120,522 | B2 | 2/2012 | Tralshawala et al. |
| 8,174,139 | B1 | 5/2012 | Parsche et al. |
| 8,553,233 | B2 | 10/2013 | Newman |
| 2001/0050772 | A1 | 12/2001 | Meinlschmidt et al. |
| 2004/0236538 | A1 | 11/2004 | Wobben |
| 2005/0157313 | A1 | 7/2005 | Mendlovic et al. |
| 2006/0181285 | A1 | 8/2006 | Friedman et al. |
| 2007/0132461 | A1 | 6/2007 | Holmquist et al. |
| 2008/0237466 | A1 | 10/2008 | Key |
| 2009/0201971 | A1 | 8/2009 | Goldammer et al. |
| 2010/0103260 | A1 | 4/2010 | Williams |
| 2010/0253569 | A1 | 10/2010 | Stiesdal |
| 2011/0020122 | A1 * | 1/2011 | Parthasarathy ......... F03D 1/003 416/61 |
| 2011/0135466 | A1 * | 6/2011 | Latorre .................... F03D 7/02 416/1 |
| 2012/0029840 | A1 | 2/2012 | George |
| 2012/0141275 | A1 | 6/2012 | Hiremath et al. |
| 2012/0253697 | A1 | 10/2012 | Frankenstein et al. |

FOREIGN PATENT DOCUMENTS

| | | | |
|---|---|---|---|
| EP | 2527649 | B1 | 11/2012 |
| GB | 2235604 | A | 6/1991 |
| WO | 2007085259 | A1 | 8/2007 |
| WO | 2012003372 | A2 | 1/2012 |

OTHER PUBLICATIONS

Zell, H., et al., "Wind Turbine Inspection—New Methods of Remote Non-destructive Inspection of Rotorblades", Dewi Magazin No. 40, pp. 14-22 (Feb. 2012).

Anjar, B., et al., "Feasibility Study of Thermal Condition Monitoring and Condition based Maintenance in Wind Turbines", Elforsk Electricity and Power Production, Elforsk rapport 11:19, pp. 1-26 (May 2011).

Rumsey, M., "NDT, CM and SHM of Wind Turbine Blades at the National Labs", 2009 NREL Wind Turbine Condition Monitoring Workshop, Wind and Water Power Technology Laboratories, Albuquerque, NM, (Oct. 2009).

Hyers, R., et al., "Condition Monitoring and Prognosis of Utility Scale Wind Turbines", Energy Materials, vol. 1, No. 3, pp. 187-203 (Sep. 2006).

International Search Report and Written Opinion dated Jun. 11, 2014 for corresponding PCT/US2014/030189 filed Mar. 17, 2014.

Hung, Y.Y., "Shearography for Non-destructive Evaluation of Composite Structures", Optics and Lasers in Engineering, vol. 24, pp. 161-182, (1996).

Meinlschmidt, P., et al., "Thermographic Inspection of Rotor Blades", ECNDT 2006—Tu.1.5.3 (2006).

Leblanc, B., et al., "Full-Field Inspection of a Wind Turbine Blade Using Three-Dimensional Digital Image Correlation", Industrial and Commercial Applications of Smart Structures Technologies 2011, Proceedings of the SPIE, vol. 7979, pp. 79790L-79790L-12, (Mar. 2011).

Bond, L., et al., "Condition Monitoring Techniques for Composite Wind Turbine Blades", Review of Progress in Quantitative Nondestructive Evaluation, vol. 11B, Proceedings of the 18th Annual Review, Brunswick, ME, Jul. 28-Aug. 2, 1991, pp. 1647-1654 (1992).

Jungert, A., "Damage Detection in Wind Turbine Blades Using Two Different Acoustic Techniques", NDT.net—The e-Journal of Nondestructive Testing (Dec. 2008).

Beattie, A., "Non-Destructive Evaluation of Wind Turbine Blades Using an Infrared Camera", American Institute of Aeronautics and Astronautics, AIAA 99-0046, (1998).

Renshaw, J., et al., The Sources of Heat Generation in Vibrothermography, NDT & E International, vol. 44, Issue 8, pp. 736-739 (Dec. 2011).

Rumsey, M., et al. "Structural Health Monitoring of Wind Turbine Blades".Smart Sensor Phenomena, Technology, Networks, and Systems 2008. Proceedings of the SPIE, vol. 6933, article id. 69330E (2008).

* cited by examiner

NONDESTRUCTIVE ACOUSTIC DOPPLER TESTING OF WIND TURBINE BLADES FROM THE GROUND DURING OPERATION

Applicant hereby incorporates by reference, as if set forth fully herein, the entirety of the disclosures of U.S. Nonprovisional patent application Ser. No. 13/731,085, filed Dec. 30, 2012; U.S. Nonprovisional patent application Ser. No. 13/837,145, filed on Mar. 15, 2013; and U.S. Nonprovisional patent application Ser. No. 13/839,908, filed on Mar. 15, 2013.

BACKGROUND OF THE INVENTION

1. Field of the Invention

The invention relates to a method and apparatus for inspecting wind turbine blades and power generating equipment in rotating wind turbine generators.

2. Description of the Related Technology

Due to their large size and extensive surface area and complex shape, wind turbine blades are difficult to non-destructively inspect even in the factory. Visual inspection does not see defects below the surface. Active thermography inspection techniques are effective for near surface defects but can give false positives and false negatives due to variations in material thickness and surface emissivity. Angle beam ultrasonic techniques are very slow and may not work through thick carbon fiber spar caps. As a result, blades are installed on towers and put into service with a significant probability of latent manufacturing defects.

Furthermore, composite blades are subject to extreme temperature variations. Entrapped water in blades can undergo freeze/thaw cycles causing internal damage. Cyclic forces of gravity and varying forces from the wind acting on the blades as they rotate can cause fatigue damage or the propagation of latent defects over time while manufacturing process mistakes can lead to early blade failure. Defects can grow below the surface of blades to the point that by the time cracks and damage breach the surface and can be detected visually, the damage may not be repairable on tower.

Detecting progressive subsurface damage and propagating defects in wind turbine blades in situ is difficult. Inspectors using sky cranes or rope access are expensive, time consuming and put personnel in a very dangerous working environment. Access with portable instruments for nondestructive testing again requires rope access or sky platforms and cranes. Blade and tower crawlers with nondestructive testing sensors for in situ inspection have been developed and tested, with high cost implications, slow inspection rates and questionable effectiveness. While on tower, close access allows inspectors to visually detect such blade defects as trailing edge splits, cracks, lightning damage and blade erosion.

There accordingly exists a growing need for a fast, cost effective nondestructive inspection methods for wind turbine blades to detect these and other anomalies.

SUMMARY OF THE INVENTION

Accordingly, it is an object of the invention to provide a fast, cost effective nondestructive inspection methods for wind turbine blades to detect these and other anomalies.

In order to achieve the above and other objects of the invention, an apparatus for inspecting rotating wind turbine blades according to a first aspect of the invention includes a microphone that is positioned approximately in a plane of a turbine disk at a point under a lowest level of a blade tip as its rotates, so as to to receive acoustic signals emanating from air escaping through breaches in a blade outer mold line from an interior or subsurface defect in the blade; and a system for analyzing the acoustic signals thus received in order to detect the presence of a potential defect.

A method of detecting an anomaly in a rotating wind turbine blade according to a second aspect of the invention includes steps of monitoring acoustic emissions from a wind turbine blade; and performing a Doppler analysis on the acoustic emissions in order to identify an anomaly in the wind turbine blade.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
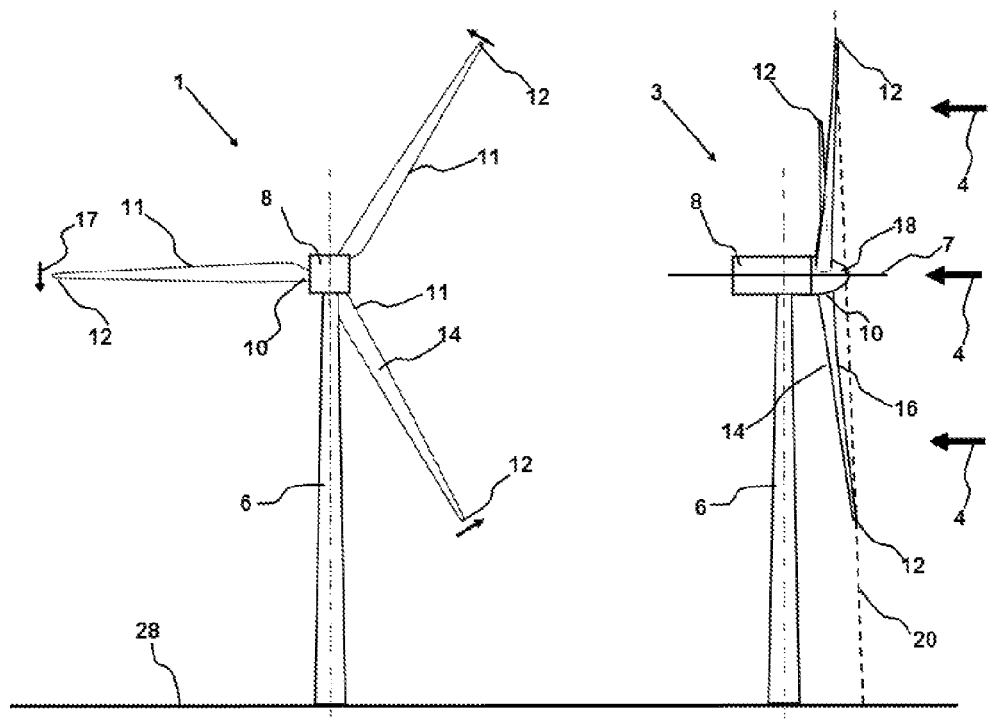
FIG. 1 is a schematic representation of a utility scale, horizontal axis, wind turbine generator.

A method and apparatus for the nondestructive testing of horizontal axis wind turbine (HAWT) blades during operation is described herein. The system and method described below permits the detection and location of anomalies in wind turbine blades by detecting and analyzing the acoustic signals generated by the blade as it moves through the air and by sound emitted when the compressed air inside the turbine blade escapes through breaches in the outer mold line of each blade. Such turbine anomalies as cracks, trailing edge splits, lighting holes, damage, blade erosion and improper blade pitch angle can be detected in seconds and in many cases their location on the blade may be determined. In addition, anomalies or condition changes in the turbine generator machinery in the nacelle may be detected from the ground. Such information has significant commercial potential for optimal wind power asset management and maintenance scheduling to reduce cost.

As the wind turbine blades are rotated through the air, sound is generated by multiple sources. First, air inside the operating wind turbine blades is compressed towards the blade tip due to the centripetal acceleration. Even with water drain holes, cracks and trailing edge splits are revealed by the sounds they emit. These acoustic signals, as recorded from the ground near the base of the tower, are Doppler shifted allowing the calculation of the defect distance from the turbine axis or the blade root end. Second, the broad band acoustic signature of air turbulence with each blade pass monitored from the ground or sea level with a sensitive wide band microphone may be analyzed with a spectrum analyzer to reveal patterns consistent with blade erosion or a blade pitch angle that is incorrect for the wind speed or direction indicating faulty sensors or a problem with the pitch actuator.

The preferred embodiment includes a microphone sensitive over a broad frequency range from 100 Hz. to 80 kHz., a computer with software to analyze the acoustic signals generated by the blade as it moves through the air and by sound emitted by air escaping through cracks, holes and breaches in the blade outer mold line. A still or video camera, triggered by the computer, by time signals or manually by the operator based on the real time spectrogram is used to identify the blade serial number for any blade with an anomaly. Noise due to abnormal turbulence caused by blade distortion, erosion and improper pitch angle is also detected and can be compared with tests taken on a periodic basis to identify trends and changes to the blades. In addition, anomalies or condition changes in the turbine generator machinery in the nacelle and in the hub, such as the blade pitch actuators, some of which operate continuously as the turbine rotates, can be detected from the ground.

Wind turbines normally operate with blade tip speeds that are many time greater than the wind speed. For example a typical 2.3 MW turbine generator (Siemens Model SWT-2.3-101) with 49 m long blades and a hub diameter of 3 m has a swept circumference at the blade tip of C=π×101=317.3 m. At a typical operating speed of 15 rpm, tip speed Vt=317.3 m×15 rpm=4759.5 m/minute or by dividing by 60, 79.3 m/second (260.2 ft/sec. or 177.4 mph). This turbine generator has a typical cut-in wind speed of 3-4 m/sec and produces nominal rated power output at 11 m/sec., a wind speed only 13.8% of the tip velocity. The rotation velocity for any location on a blade may be expressed as $V_L=2\pi L/\tau$, where L is the distance from the turbine axis and $\tau$ is the period of rotation of the turbine in seconds. This linear equation allows the calculation of air pressure inside a rotating blade and as we will show, can be used to determine the location of sound emitting defects on rotating turbine blades, $L_D=L-H_R$, where $L_D$ is the defect distance from the blade root, L is the distance of the defect from the turbine axis and $H_R$ is the radius of the turbine hub.

A hollow, rotating wind turbine blade acts to compress the air column within the blade towards the blade tip due to the centripetal acceleration. This increased air pressure at the tip and can be calculated as:

$$P_x = P_{atm} \left| \frac{1}{2} \rho \omega^2 x^2, \right. \quad \text{Equation 1.}$$

where $\rho$ is the density of air $\omega$ is the speed of rotation of the turbine $\chi$ is the distance from the blade tip to the turbine axis.

As the blade rotates and the contained air volume is compressed, a partial vacuum forms at the root end of the blade drawing air into the blade through gaps at the edges of the man-way cover plate bolted to the blade root end bulkhead. The compressed air escaping through shell cracks and splits in adhesive bonds along the leading and trailing edges create a whistling tone, that may be detected from the ground. Even with water drain holes present in the blade tips, air pressure will build up inside the rotating blades. It has long been known that larger blade cracks and splits often create strong acoustic signals during turbine operation that are easy to hear especially from the top of the nacelle. A wind turbine maintenance worker hearing a turbine whistle knows a blade is cracked but he does not know which blade or blades are defective, how many defects are present or where they are located. Further, other defects may emitted acoustic signals with low amplitude or at frequencies beyond the range of human hearing. The system disclosed herein detects these acoustic signals from the ground using the Doppler shift to determine the distance location.

The broad band microphone is used to detect the acoustic signal emitted from blade defects, which may have a significant component in the ultrasonic range above the range of human hearing. The rotation of the blade Doppler shifts the emitted frequency from the defect so as the blade is approaching the sound received at the microphone is higher than the actual emitted tone. As the blade recedes from the microphone, sound of the emitted tone the as received at the microphone is Doppler lower. Using the equations derived herein, the distance from the crack or anomaly to the blade hub may be calculated. Further, the system detects the Doppler shifted acoustic signature emitted from changes to the blade surface due to erosion and also the signals from air turbulence when a blade is operating at the incorrect angle of attack. Finally this invention teaches several means to identify the specific blade serial number.

To perform an acoustic test on operating wind turbine blades, microphone is positioned near the tower and held by hand or mounted on tripod. The position is not critical, but should within 3-5 m, up or down wind of the plane containing the turbine blade tips and within about 50% of the a blade span from the tower base. The microphone may be attached to a tripod or to a vehicle (land or water), with a clear unobstructed view to the blade disk, for quick movement from one tower to the next during a site inspection.

The microphone provides a signal to the sound card the computer which contains both audio recording capability and the acoustic spectrum analysis software. The system software may operate manually or be complete automatic. The test is conducted by first setting the signal gain of the acoustic signal for the passage of the blades. The spectrum analyzer will display the full spectrum of the signal and the maximum frequency can be adjusted to provide optimal resolution of the acoustic signal spectrum. The first measurement is to determine the period of the turbine in seconds which is the time in seconds from a first blade pass signal peak until the same peak repeats on the fourth blade pass signal. The operator can use the graphical image interface by stopping the spectrum display and measure the time in seconds between four peaks on the spectrum display. In real-time or when a full period spectrum is frozen on the screen, signals from defects appear, with possible overtones, as a wavy lines in the spectrum on top of the aerodynamic noise produced by the blade as it passes overhead. The signal from the defect is a steady frequency or tone, if you are in the frame of reference as the blade (theoretically riding with the blade) or listening from the turbine nacelle close to the turbine axis. The acoustic signal from a blade defect as heard from the tower base on the ground or floating in a boat next to an off-shore turbine tower the signal is Doppler shifted making the whistle go from a high frequency tone as blade moves down towards the microphone to a lower frequency tone or whistle as the blade move away from the microphone. Measuring the maximum and minimum Doppler shifted frequencies of defect indications can be done using the spectrum display on the graphical user interface or can be accomplished automatically by the software. Knowledge of the air temperature can be entered manually into the computer or measured with a sensor to determine the speed of sound in the air from a store look up table or calculation at the turbine tower when the data is collected. The error due to air density changes with altitude or barometric changes is generally much smaller than other errors caused in the spectral measurements and is not generally considered.

For offshore wind turbines, it may be advantageous to install the microphone permanently on the tower, above the level of expected wave action. Data can be transmitted via radio of cellar CSM to a receiver on shore. The entire unit can be solar powered using a small array of photovoltaic cells and a rechargeable battery. Installing two or more microphones at different heights would allow better acoustic coverage of the large towers anticipated for off shore towers and better accuracy in defect location.

The shape of the modern turbine blades is a highly refined super-critical airfoil. Blade delaminations in the composite surfaces as well as weak, broken or non-existent spar cap to spar web bonds allow increased blade twist or blade bending during operation changing air flow and air turbulence noise. In addition, deviations from the correct blade pitch angle from nominal values can initiate the onset of turbulence and generate noise. Damage to the blade from lightning, cracks at the blade surface changing the surface profile, delaminations changing the blade cross section profile may cause noise due to turbulence and changes air flow over the blade surfaces. The acoustic signature for a blade may be change significantly. In addition, a lack of bond between the spar web and the spare cap can allow the blade to bend more during the rotational cycle due to varying gravitational force and wind pressure loading than other blades again changing the acoustic signature.

The test method and apparatus described here may be used also for periodic checks to detect changes in the acoustic spectrogram, signal intensity and Doppler shift of signals by which defect locations can be determined. To determine the span wise location of a sound emitting defect on a blade we need to measure:

$\tau$=turbine period, sec.
$F_H$=Maximum Defect Doppler Shifted Frequency
$F_L$=Minimum Defect Doppler Shifted Frequency
T=air temperature From the geometry of a rotating wind turbine, the emitted frequency of the defect $F_0$, can be determined as the average of the high and low Doppler shifted frequencies for the signal, as shown in Eq. 2.

$$F_0 = (F_H + F_L)/2 \qquad \text{Equation 2}$$

The tangential velocity of a blade defect, $V_D$, at distance L from the turbine hub, for a turbine with a period $\tau$, seconds can be expressed as shown in Eq. 3:

$$V_D = 2\pi L/\tau, \text{ solving for } L: \qquad \text{Equation 3}$$

$$L = V_D \tau / 2\pi \qquad \text{Equation 4}$$

From the Doppler equation, $F_L$, the Doppler shifted low frequency signal is:

$$F_L = F_0 V_S / (V_S + V_D), \qquad \text{Equation 5}$$

where $V_S$ is the speed of sound at the tower.
Since most wind turbines are located at an altitude of less than 5,000 ft., above sea level, $V_S$ can be determined from a lookup table corrected for the temperature at the tower, although any means for accurate determination of $V_S$ may be used.
$F_H$, the Doppler shifted high frequency signal is:

$$F_H = F_0 V_S / (V_S - V_D), \qquad \text{Equation 6}$$

substituting Equation 2. for $F_0$, we obtain $$F_H = \frac{(F_H + F_L) V_S / (V_S - V_D)}{2}. \qquad \text{Equation 7}$$

Solving for $V_D$, we obtain $$V_D = \frac{2 V_S F_H + 2 V_S F_L}{4 F_H}. \qquad \text{Equation 8}$$

Substituting Equation 3. for $V_D$, we obtain, $$\frac{2\pi L}{\tau} = \frac{2 V_S (F_H - F_L)}{4 F_H}. \qquad \text{Equation 9}$$

Solving for L, the distance from the turbine axis to the defect, we obtain, $$L = \frac{\tau V_S (F_H - F_L)}{4 \pi F_H}. \qquad \text{Equation 10}$$

The distance from the blade root end to the defect then is, $$L_D = L - R_H, \qquad \text{Equation 11}$$

where $R_H$ is the radius of the turbine hub

FIG. 1, is a schematic diagram of a HAWT that is typical of both land based and off-shore turbine generators. The view 1 from behind the turbine facing the wind includes tower 6 extending up from the ground or ocean surface 28 to support the nacelle 8 which contains the generator and gear reducers, unless it is a direct drive generator. Note that if this invention is used on a ship to test off shore wind turbine blades, 28 would be that deck of the ship from which the testing is performed. Wave motion generally would have velocity components too small to significantly affect the Doppler shifted frequency measurements. There are typically three blades, 11, on a utility scale wind turbine having root ends 10 and blade tips 12. As seen from the side view 3, the blade root ends attach to the rotatable hub 18. Blade side 16 facing the wind 4 is often referred to as the high pressure side. The blade side 14, facing away from the wind is referred to as the low pressure or suction side. As the blade speed 17 increases, the blade pitch is adjusted to the optimal angle of attack to the wind 4 to create the maximum lift and torque required to drive the electricity generator.

Figure 2:
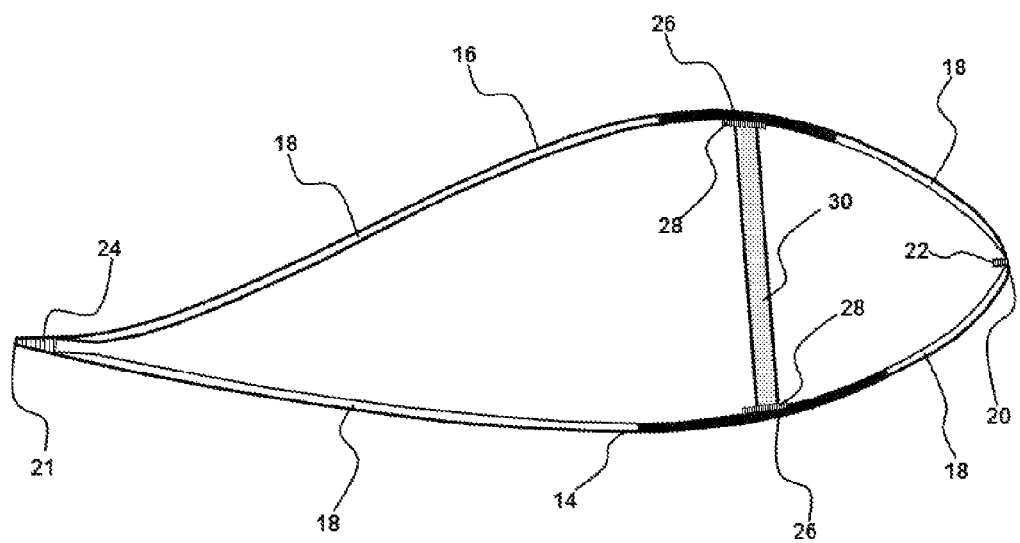
FIG. 2 is a schematic representation of a wind turbine blade cross section.

FIG. 2 shows the construction cross section of a typical HAWT blade. Wind turbine blades are generally manufactured with adhesively bonded composite shells forming the high pressure side 16 and the low pressure side 14. The trailing edge 21 is formed by the adhesively bonded shells 14 and 16 as is the leading edge 20, with adhesive bonding in some cases between two flanges 22 formed by the inner and outer fiberglass skins that make up sandwich panels 18. Two spar caps 26, which may be made from fiberglass or carbon fiber laminate or other composite material, are bonded to the edges of the sandwich panels 18. The blade spar web 30, which can be a solid fiberglass laminate or a sandwich construction with fiberglass or carbon fiber face sheets and a core material made with foam, balsa wood or other suitable material with high compressive strength. The spar web 30 is bonded with adhesive 28 to the spar caps 26 to form an I beam. Sometimes a second or even third spare web is present forming a box beam. Defects such as adhesive disbonds or unbonds present at the spar cap 26 to spar web 30 adhesive bond 28 may lead to catastrophic failure of the blade in service. Fiber waves in the solid spar cap 26 laminate can also lead to cracking and ultimately to blade failure. Further, trailing edge 21 splits or cracks in the high pressure 16 and low 14 pressure side shell adhesive bond 24 may be signs or excessive blade flex during operation. The trailing edge 21 adhesive bond 24, in the area of greatest blade chord width towards the root end 10 supports blade twist loads. Cracks and breaks in the adhesive bond 24 at these locations can also lead to blade failure unless detected in time and the turbine shut down and promptly repaired.

Figure 3:
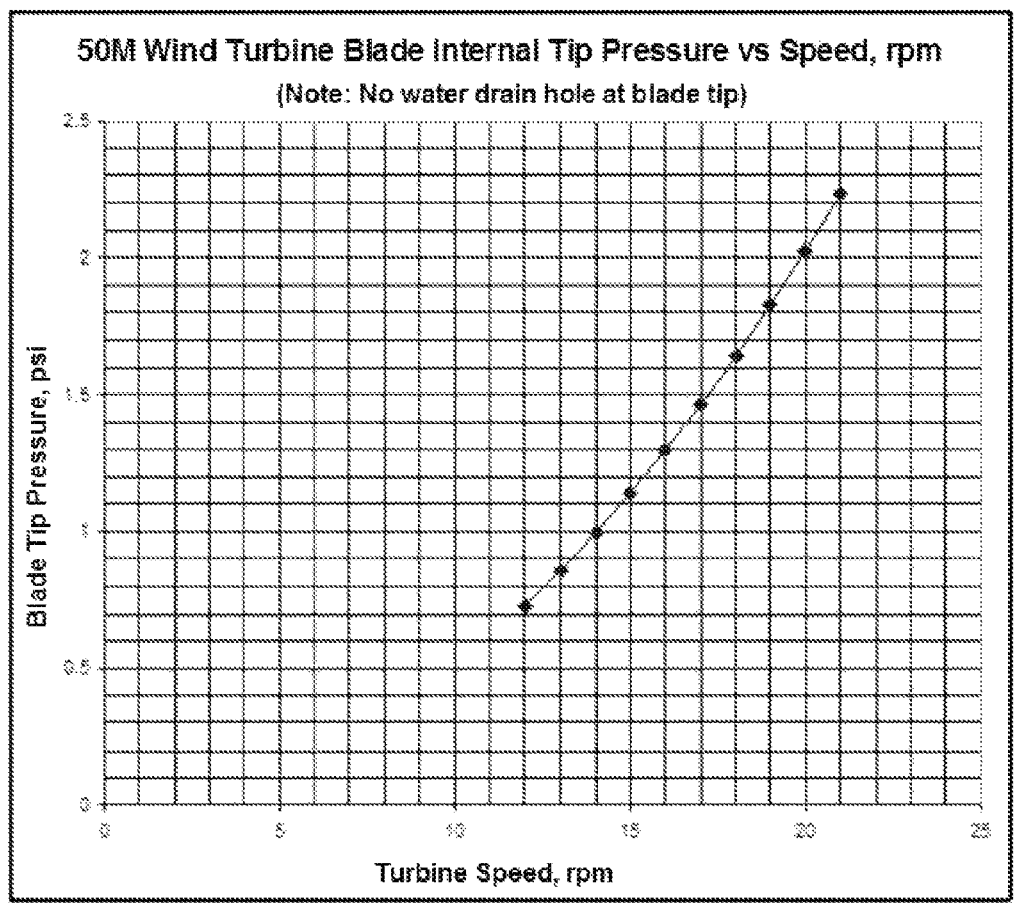
FIG. 3 is a graphical depiction of internal tip pressure versus speed.

FIG. 3 is a plot showing the increase in air pressure inside a 50 m turbine blade as a function of the rotation speed in rpm., not including the effect of gravity, which would add a (k) cos θMG term to the air pressure, where k is a constant that diminishes with increased turbine RPM. M is the mass of the air inside the blade and G is the acceleration due to gravity. FIG. 3 depicts the internal blade pressure above ambient at the outboard tip of a 50 meter long blade rotating speed from 12 to 21 rpm, neglecting the presence of the water drain hole at the blade tip. For a sealed blade, the pressure reduction below ambient on the inside of the root end bulkhead would be the negative of these values.

Figure 4:
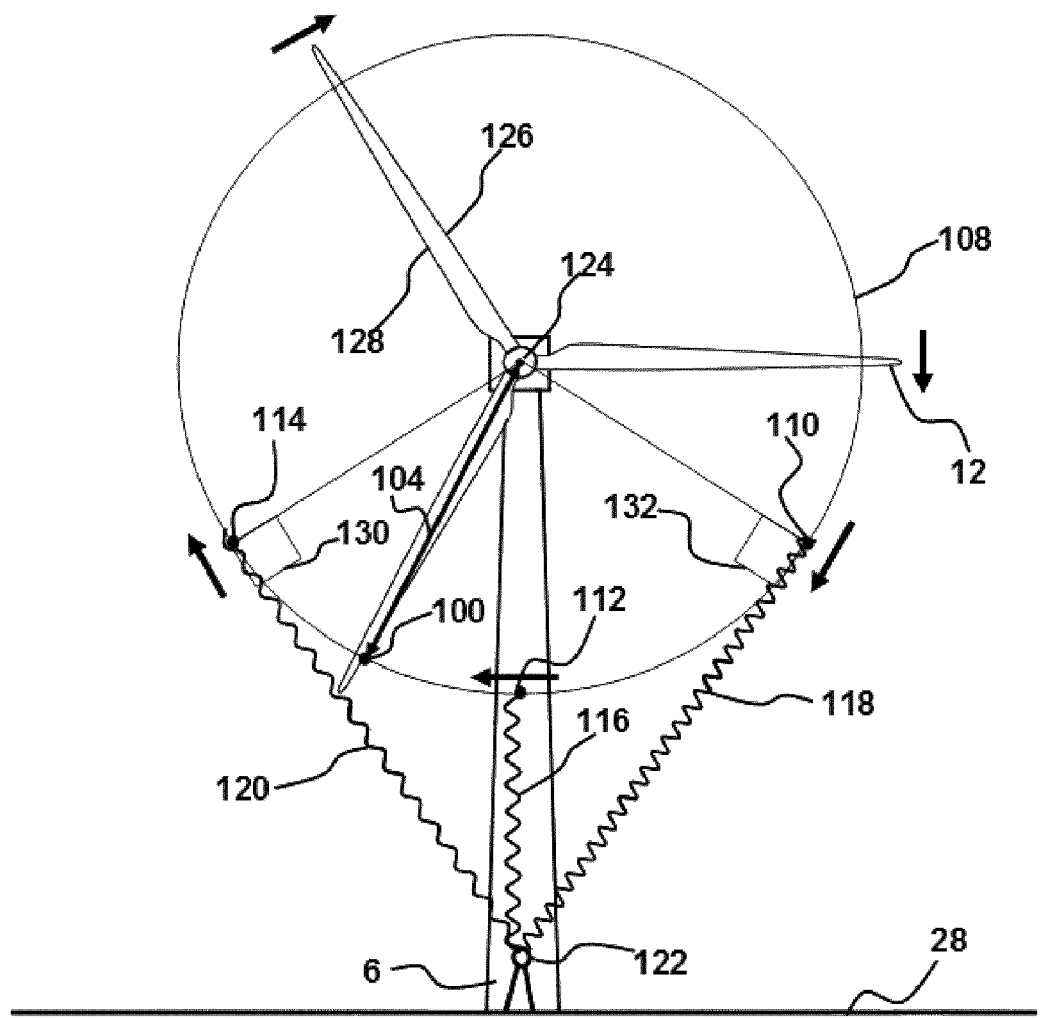
FIG. 4 is a schematic depiction showing a wind turbine tower with three blades and a defect.

FIG. 4 shows a schematic of the showing the wind turbine tower 6, with three blades and a defect 100, located on one blade a distance 104 from the turbine axis 124. The defect rotates clockwise (as seen from the front of the turbine) in a circle 108 with diameter 104. Emitting a tone at frequency 116, the defect signal is Doppler shifted high to frequency 118, when it is approaching microphone 122 at the base of tower 6. The signal frequency is a maximum high when the defect is at position 110, on a line 118, tangent to circle 108 and microphone 122. Like wise, the minimum frequency of the defect signal due to the Doppler shift is when it is receding from the microphone 122 at the base of tower 6. The signal frequency is shifted to a minimum low 120, when the defect is at position 110, on a line tangent to circle 108 and microphone 122.

Figure 5:
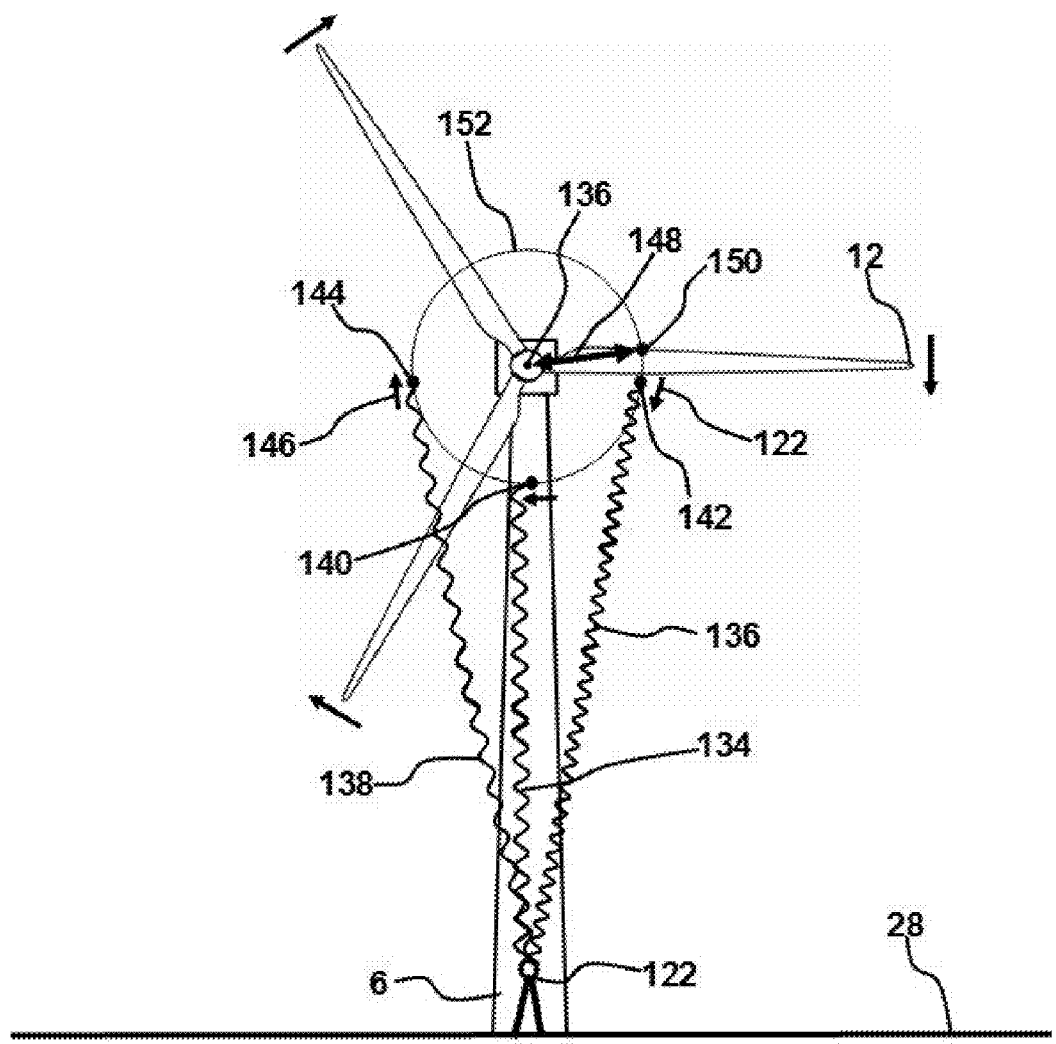
FIG. 5 shows a plan view of a wind turbine site with six locations.

FIG. 5 shows the similar geometry as FIG. 4, but for a defect 150, located a closer distance 148 from the turbine axis 136. Because of the shorter distance 148, than for defect 100, the resulting difference between the Doppler shifts, 134 and 138 is significantly less.

Figure 6:
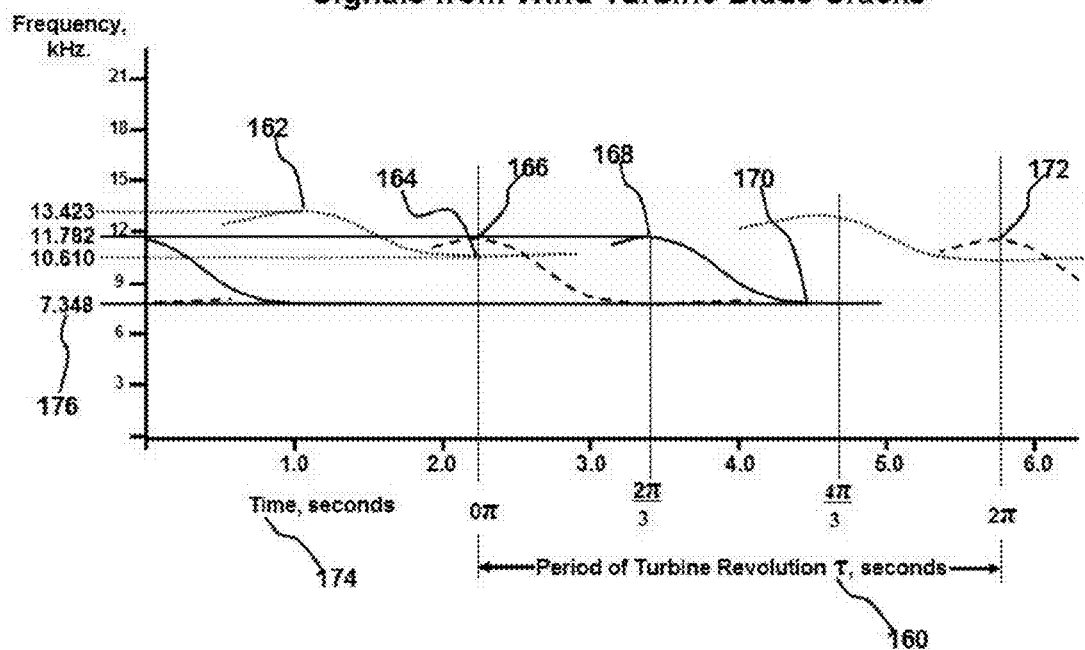
FIG. 6 is an acoustic spectrogram showing three sound emitting defects in a wind turbine blade.

FIG. 6 shows an acoustic spectrogram of three sound emitting defects, one each in the three blades on a 1.5 MW turbine. The period 160 of the blade can be measured by the time between the repeating peak frequency signals 166 and 172, from the same defect.

The minimum 164 and 170 and maximum 162 and 168 Doppler shifted frequencies for two of the defect signals are shown and can be measured with the spectrometer.

These values can be used to calculate the location of the defect along the blade.

Figure 7:
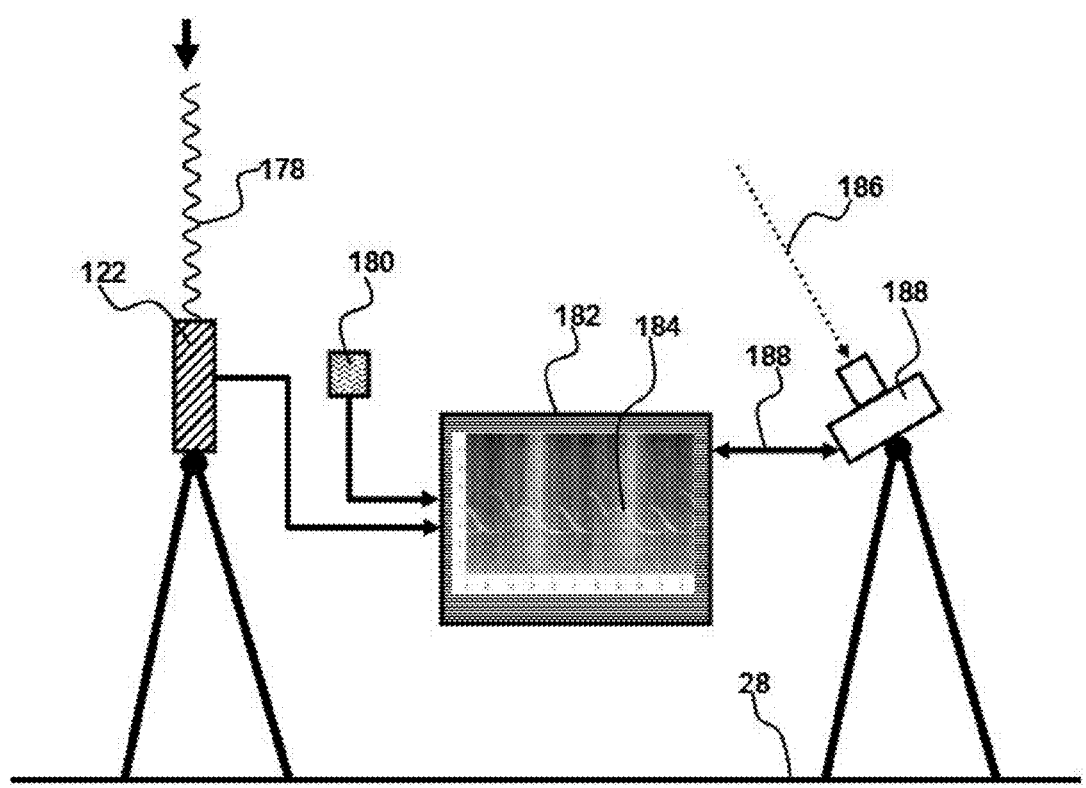
FIG. 7 is a schematic depiction of a system for performing an acoustic spectral test of a wind turbine blade set according to a preferred embodiment of the invention.

FIG. 7 shows a schematic diagram of the equipment for performing an acoustic spectral test of a wind turbine blade set. Sound 178 enters the microphone 122 which provides a signal to the sound card in computer 182. Temperature sensor 180, provides the air temperature reading to the computer to determine the velocity of sound in the air at the turbine site. This temperature value can also be entered manually. The spectrogram is displayed on the monitor 182 in real time. Blades with anomalies can be used to manually trigger, by remote control, camera 188, to capture the light forming the image of the blade serial numbers 186. In another embodiment, GPS time signals can be recorded on the sound track of a video camcorder and also to time stamp the Doppler shifted signals, to identify the blade with the defect. Another camera trigger can be established using the real time spectrogram. The spectrum can be stopped and the blade with the defect signal identified on the computer screen using a mouse or a touch screen feature if present. The spectrum can be restarted acquiring new signals using the same time base. The computer would the send a signal to trigger the serial number camera every time that blade come into the field of view.

Figure 8:
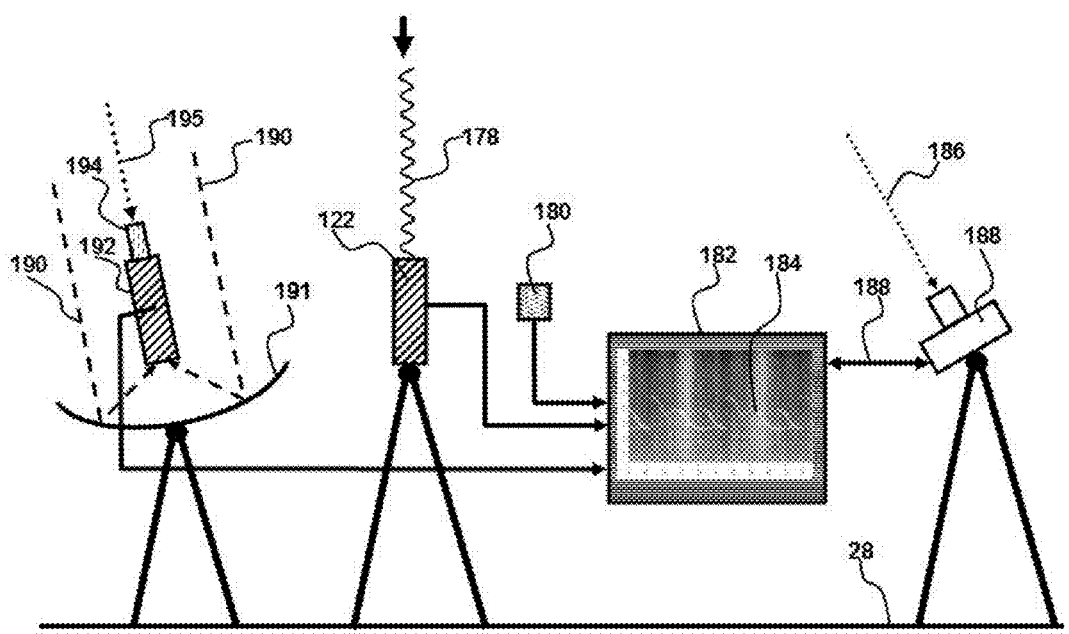
FIG. 8 is a schematic depiction of the system shown in FIG. 7 in operation.

FIG. 8 is a schematic for an equipment set up with the inclusion of a parabolic dish reflector 191, to receive signals 190 from machinery in the hub or nacelle for analysis. This dish receives signals from a narrow cone and is aimed using optical sight 194, which may also be a video camera. Mounted on a vehicle or tripod, this may be aimed by remote control using motor drives in azimuth and elevation. The dish 191, may also be used to detect distant signals from near the turbine hub from defects on the blades. Generally, the signals from the blade tips may be outside the cone angle of sensitivity for the dish. A dish 191 having a removable microphone 122 would allow one microphone to be used for both near and far defect signals.

Figure 9:
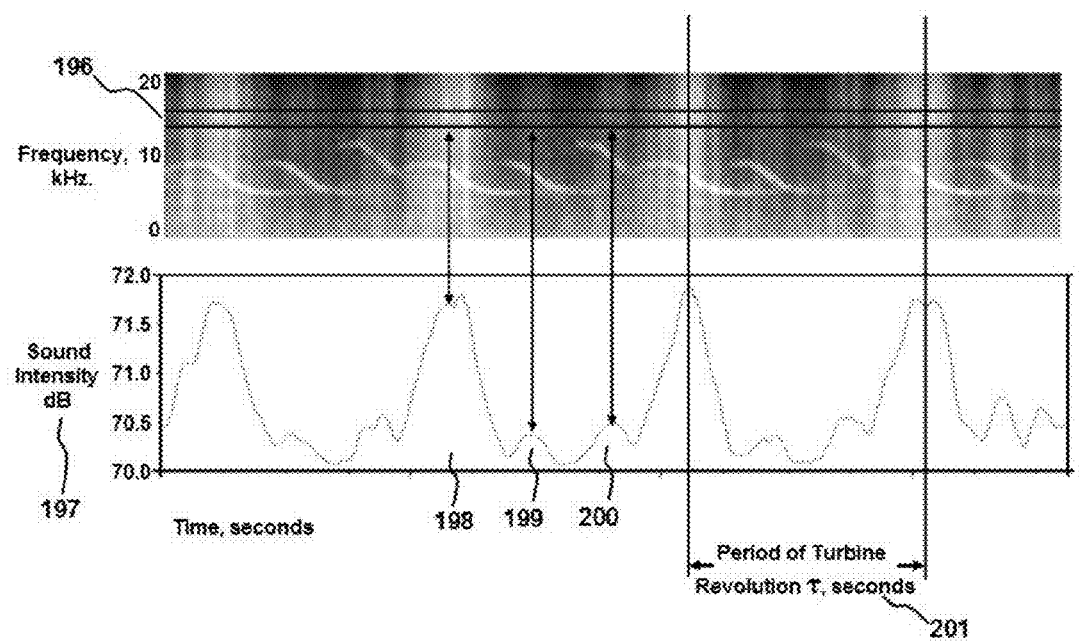
FIG. 9 is an acoustic spectrogram showing the intensity of sound over time as wind turbine blades pass an acoustic sensor.

FIG. 9 is a spectrogram with a line scan 196, showing the intensity of the sound 197, over time as the blades pass the microphone 122. The graphic display shows the sound intensity is grey level values. Black is no sound, white is the peak intensity measured. The Acoustic intensity plot 198 for one blade, is considerable greater than the plot 199 and 200 for the other two blades. The blade with intensity plot 198, had a defective blade pitch angle actuator. The blade was not set for the proper pitch angle and the sound plot 198 was the result of the turbulence in the air and resulting drag, diminishing the turbine efficiency. Causes of the improper pitch angle may be a fault with the blade pitch actuator, control circuit or a defective blade pitch bearing.

The test method and apparatus described here may be used also for periodic checks to detect changes in the acoustic spectrogram, signal intensity and Doppler shift of signals by which defect locations can be determined. In addition, the acoustic spectrum of the turbine generator bearings, gear reducers, blade pitch actuators and other machinery components can be examined for changes over time indicative of component deterioration or failure. This information is important for optimal wind power asset management, maintenance scheduling or shutting down the turbine to prevent further damage, injury or even catastrophic failure.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An apparatus for inspecting rotating wind turbine blades, comprising:
 a microphone positioned approximately in a plane of a turbine disk at a point under a lowest level of a blade tip as its rotates, so as to receive acoustic signals emanating from air escaping through breaches in a blade outer mold line from an interior or subsurface defect in the blade; and a computer for analyzing the received acoustic signals to detect the presence and location of a potential defect, relative to a root end of the blade, based at least in part on a difference between maximum and minimum defect Doppler shifted frequencies of the received acoustic signals.

2. An apparatus for inspecting rotating wind turbine blades according to claim 1, wherein the computer includes a display that displays a spectrogram.

3. An apparatus for inspecting rotating wind turbine blades, comprising:

a microphone positioned near a rotating wind turbine and configured to receive sound signals emitted by anomalies in a wind turbine blade;

a signal recording device configured to record the received sound signals; and a computer for analyzing the received sound signals by determining maximum and minimum defect Doppler shifted frequencies of the received sound signals and calculating the position of the anomalies in or on the rotating wind turbine blade with respect to a root end of the blade, based at least in part on a difference between the maximum and minimum defect Doppler shifted frequencies.

4. An apparatus for inspecting rotating wind turbine blades according to claim 3, wherein the computer is further constructed and arranged to measure a rotating blade acoustic spectrum.

5. An apparatus for inspecting rotating wind turbine blades according to claim 3, wherein the computer is further constructed and arranged to measure the relative sound level of acoustic emissions from each blade during rotation to detect changes due to blade surface profile changes.

6. An apparatus for inspecting rotating wind turbine blades according to claim 3, wherein the computer is further constructed and arranged to measure changes in airflow due to structure defects in the blade.

7. An apparatus for inspecting rotating wind turbine blades according to claim 3, wherein the computer is further constructed and arranged to measure missing or peeling leading edge protection tape.

8. An apparatus for inspecting rotating wind turbine blades according to claim 3, wherein the computer is further constructed and arranged to measure damage to the blade composite materials.

9. An apparatus for inspecting rotating wind turbine blades according to claim 3, further comprising a camera for photographing blade serial numbers.

10. An apparatus for inspecting rotating wind turbine blades according to claim 9, wherein the camera is triggered by spectrogram software.

11. An apparatus for inspecting rotating wind turbine blades according to claim 10, wherein the camera is synchronized with GPS signals to identify the blade with a detected anomaly.

12. An apparatus for inspecting rotating wind turbine blades according to claim 3, wherein the microphone includes a parabolic reflector and an optical aiming device.

13. A method of detecting an anomaly in a rotating wind turbine blade, comprising steps of:

monitoring acoustic emissions from a wind turbine blade; and performing a Doppler analysis on the acoustic emissions in order to identify and locate, relative to a root end of the wind turbine blade, an anomaly in the wind turbine blade, the Doppler analysis including at least a determination of maximum and minimum defect Doppler shifted frequencies.

* * * * *